United States Patent [19]

Murata et al.

[11] Patent Number: 4,523,142

[45] Date of Patent: Jun. 11, 1985

[54] APPARATUS FOR SENSING DEW AND FROST

[75] Inventors: Michihiro Murata, Kyoto; Akira Kumada, Ootsu, both of Japan

[73] Assignee: Murata Manufacturing Co., Ltd., Japan

[21] Appl. No.: 424,344

[22] Filed: Sep. 27, 1982

[30] Foreign Application Priority Data

Jul. 1, 1981 [JP] Japan .................................. 56-103854

[51] Int. Cl.³ .......................................... G01R 27/02
[52] U.S. Cl. .................................................. 324/65 R
[58] Field of Search .............. 324/65 R, 65 P; 338/34, 338/35; 73/29, 73; 340/602, 601

[56] References Cited

U.S. PATENT DOCUMENTS

| | | | |
|---|---|---|---|
| 2,435,895 | 2/1948 | McIlaine | 324/65 R X |
| 3,226,610 | 12/1965 | Harman, Jr. et al. | 338/35 X |
| 3,696,360 | 10/1972 | Gajewski | 340/602 |
| 3,757,212 | 9/1973 | Johnson | 324/65 R |
| 3,873,927 | 3/1975 | Overall | 324/65 P |
| 4,023,094 | 5/1977 | Adams | 324/65 R |
| 4,227,411 | 10/1980 | Abramovich | 338/35 X |
| 4,270,085 | 5/1981 | Terada et al. | 324/65 R |
| 4,272,986 | 6/1981 | Lowry et al. | 324/65 R X |
| 4,281,286 | 7/1981 | Briggs | 324/65 R X |

Primary Examiner—Stanley T. Krawczewicz
Attorney, Agent, or Firm—Ostrolenk, Faber, Gerb & Soffen

[57] ABSTRACT

An apparatus for sensing dew and frost, comprising a sensing portion which includes a substrate (1) having less permittivity than ice and includes a pair of electrodes (2, 3) 5 arranged to touch the substrate (1) and further includes a resistive film (4) on the substrate (1) covering the pair of electrodes (2, 3), the impedance between the pair of electrodes (2, 3) changing in three states, or dry, bedewed and frosted states.

9 Claims, 11 Drawing Figures

APPARATUS FOR SENSING DEW AND FROST

BACKGROUND OF THE INVENTION

1. Fields of the Invention

The present invention relates to an apparatus for sensing three states, dry, bedewed and frosted states in the form of the change of an electric signal.

2. Description of the Prior Art

Since the control of humidity is very important matter in various kinds of electric apparatuses, it is desired that an excellent humidity sensor is realized. Moreover, for a particular apparatus, the reduction of the function thereof by frost is a serious matter, in addition to the reduction of the function thereof by dew. Since, in a freezer, for example, the generation of frost causes the efficiency thereof to be reduced, the frost needs to be eliminated. Therefore, it is desired that a sensor capable of detecting the frosted state is realized.

Hithereto, various types of dew sensors have been realized, one of them utilizing the change in the value of resistance by dew. On the other hand, as frost sensors, there were a type of the sensors utilizing the change in a resonance frequency of a resonating member caused by the frost adhering thereto, and so on. However, there was not a sensor which was of a simple element and could detect both of dew and frost, more accurately all of three states, or dry, bedewed and frosted states. In other words, the apparatus needed at least two detecting elements in order to detect all of the above described three states, dry, bedewed and frosted states, and thus more complicated configuration thereof was needed in order to do so.

SUMMARY OF THE INVENTION

The present invention, in summary, is an apparatus for sensing three states, dry, bedewed and frosted states, comprising:

a sensing element including a base material having a permittivity which is less than the permeativity of ice and a pair of electrodes coupled to said base material at spaced locations thereof, the impedance of said sensing element as measured across said electrodes varying as a function of whether said sensing element is in the dry, bedewed or frosted states, said impedance being at a maximum value when said sensing element is in the dry state, said impedance being at a middle value lower than said maximum value when said sensing element is in the frosted state, said impedance being at a minimum value lower than said maximum and middle values when said sensing element is in the bedewed state; and means for measuring the impedance between said electrodes and generating electric signals indicative of whether said sensing element is in the dry, bedewed or frosted state.

A preferred embodiment the measuring means comprises: first reference level setting means for setting a first reference level which resides between the middle value and the minimum value of the impedance between the electrodes of said sensing portion; second reference level setting means for setting a second reference level which resides between the middle value and the maximum value of the impedance between the electrodes of said sensing portion; first comparing means for comparing said first reference level provided by said first reference level setting means with the impedance between the electrodes of said sensing portion; second comparing means for comparing the second reference level provided by said second reference level setting means with the impedance between the electrodes of said sensing portion; and determining means for determining the dry state when said first comparing means indicates that the impedance between said electrodes is higher than said first reference level and said second comparing means indicates that the impedance between said electrodes is higher than said second reference level, for determining the frosted state when said first comparing means indicates that the impedance between said electrodes is higher than said first reference level and said second comparing means indicates that the impedance between said electrodes is lower than said second reference level, and for determining the bedewed state when said first comparing means indicates that the impedance between said electrodes is lower than said first reference level and said second comparing means indicates that the impedance between said electrodes is lower than said second reference level.

The sensing element may include a ceramic substrate as the base material and the electrodes may be arranged on the ceramic substrate, or the sensing element may include a resistive film as the base material arranged on an isolating substrate and the electrodes may be arranged such that at least a part thereof is covered with the resistive film on the isolating substrate.

In a preferred embodiment, the impedance between electrodes is defined in the dry state with resistance of the base material contributing thereto most largely, defined in the frosted state with permittivity of ice contributing thereto most largely, and defined in the bedewed state with an ionic conduction phenomenon contributing thereto most largely.

In addition, the first comparing means and the second comparing means each include an operation amplifier.

Accordingly, a primary object of the present invention is to provide an apparatus for sensing dew and frost, which can detect three states, or dry, bedewed and frosted states with high accuracy by a simple element.

The above described object and other objects and features of the present invention will be more apparent from the following detailed description made in conjunction with drawings.

DESCRIPTION OF THE PREFERRED EMBODIMENTS

Figure 1:
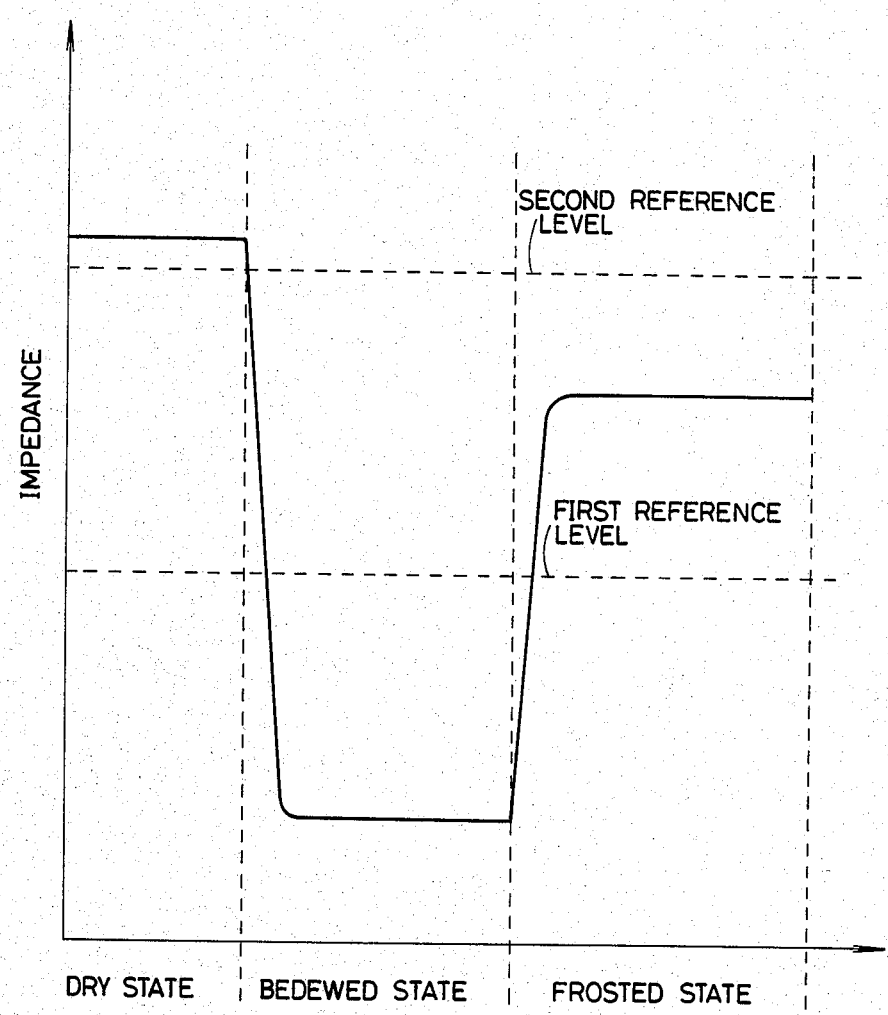
FIG. 1 is a view showing the change in impedance of a sensing element used in the present invention.

The present invention aims at utilizing a sensing element whose impedance changes at three states, dry, bedewed and frosted states. FIG. 1 is a view showing the change in impedance of a sensing element used in the present invention. As apparent from FIG. 1, a sensing element used in the present invention shows maximum impedance in the dry state, shows middle impedance in the frosted state, which is lower than that in the dry state, and shows minimum impedance in the bedewed state, which is lower than that in the frosted state. Thus, an apparatus in accordance with the present invention is structured to electrically handle such a change in the impedance of the sensing element and thereby to sense the three states, dry, bedewed, frosted states with high accuracy.

As a specified example of the base material of sensing element used in the present invention, the material may mainly include titanium complex oxide of ilmenite crystal structure such as $MgTiO_3$, $ZnTiO_3$ or $FeTiO_3$, or a dielectric substance such as a talc—$MgO$—$BaTiO_3$ system, a $BaO$—$TiO_2$—$NdO$ system of an $MgO$ $SiO_2$ system of forsterite or steatite. Preferably, by using titanium complex oxide having ilmenite crystal structure as the base material, the same can be used on the occasion of any of the alternating current and the direct current. Incidentally, on the occasion of ceramics mainly including titanium complex oxide having ilmenite crystal structure, the same may be mixed with one kind or plural kinds of ceramics having other crystal structure, such as a perovskite type, a spinel type, a pyrochlore type or a tungsten bronze type, to the extent that the properties of the same are not influenced. In addition, the same may further include various kinds of inorganic compounds, such as clay, rare earth elements, $TiO_2$, $SiO_2$, $Bi_2O_3$, $ZnO$, $Fe_2O_3$, $Sb_2O_3$, $MnCO_3$, $WO_3$ and so on.

Figure 2:
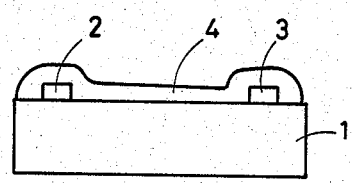
FIG. 2 is a schematically sectional view showing an example of sensing elements used in the present invention.
Figure 3:
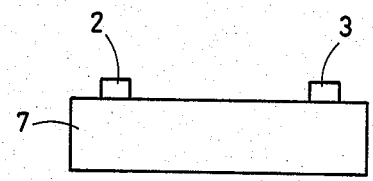
FIG. 3 is a schematically sectional view showing another example of sensing elements used in the present invention.

FIGS. 2 and 3 are sectional views schematically showing two examples of sensing elements used in the present invention.

The first example shown in FIG. 2 employs a pair of electrodes 2, 3 arranged on the upper surface of a substrate 1 serving as an isolating substrate, and a resistor 4 (the base material) arranged in a manner of a film covering the electrodes 2, 3. The change in impedance of an atmosphere including the resistor 4 is detected by the pair of electrodes 2, 3 arranged so as to touch the resistor 4.

The second example shown in FIG. 3 employs a pair of electrodes 2, 3 arranged on the upper surface of a substrate 7. The substrate 7 functions as the base material and the support substrate, in other words, the same corresponds to the substrate 1 and the resistor 4 of the example shown in FIG. 2.

Meanwhile, the sensing element used in the present invention is not restricted to the examples shown in FIGS. 2 and 3. For example, the sensing element may be structured such that a pair of electrodes are inserted into the substrate.

Figure 4:
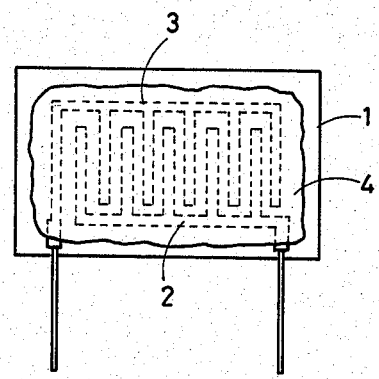
FIG. 4 is a plan view more specifically illustrating the element shown in FIG. 2.
Figure 5:
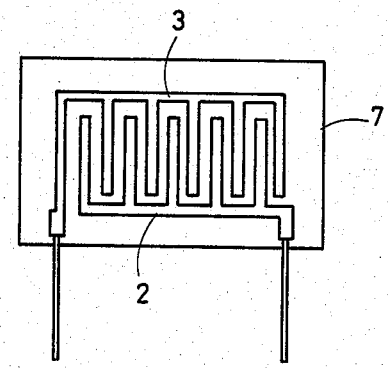
FIG. 5 is a plan view more specifically illustrating the element shown in FIG. 3.

FIGS. 4 and 5 are plan views for more specifically illustrating the above described sensing elements. More specifically, FIG. 4 is a view more specifically illustrating the example shown in FIG. 2, and FIG. 5 is a view more specifically illustrating the example shown in FIG. 3.

Referring to FIG. 4, on an alumina substrate 1 serving as the isolating substrate, there are a pair of comb-shaped gold electrodes 2, 3 having a gap therebetween (0.4 mm) and opposing length (65 mm). The resistor 4 is formed so as to cover the comb-shaped electrodes 2, 3, by paste, which comprises powder of $MgTiO_3$(96%)—$CaTiO_3$(4%) and a small quantity of mineralizer, being spread on the electrodes 2, 3, and then being sintered at a high temperature.

Meanwhile, the material of the resistor 4 formed to touch the comb-shaped electrodes 2, 3 is not restricted to the above described one. For example, inorganic polymer mainly including zirconium may be employed, which is disclosed at Japanese patent application No. 84209, filed July 10, 1978, and Japanese patent application No. 87913, filed July 18, 1978, by the same applicant as this application. In other words, any sensing elements can be used in the present invention, which have an impedance changing as shown in FIG. 1. Meanwhile, in TABLE I described later, there is shown, as Example 1, the change of impedance in case that a sensing element of the inorganic polymer mainly including zirconium is employed.

Referring to FIG. 5, on the upper surface of a ceramic substrate 7 consisting of $MgTiO_3$(96%)—$CaTiO_3$(4%), for example, are formed a comb-shaped gold electrodes 2, 3 having a gap between the electrodes (0.4 mm) and an opposing length (65 mm). As described above in conjunction with FIG. 3, the ceramic substrate 7 functions as the base material. The change of the impedance in the three states, dry, bedewed and frosted states of the element shown in FIG. 5, is shown as Example 2 in TABLE I described later. Meanwhile, the substrate 7 serving as the base material can consist of various material in this embodiment, similarly in the embodiment shown in FIG. 4.

TABLE I shows a change of the value of resistance between the electrodes on the occasion of 1V(60 $H_z$ A.C.) voltage applied therebetween.

TABLE I

| State | Example 1 | Example 2 |
| --- | --- | --- |
| Dry state | $6.5 \times 10^3$ MΩ | $1.0 \times 10^4$ MΩ |
| Bedewed state | $2.06 \times 10^2$ kΩ | $2.50 \times 10^2$ kΩ |
| Frosted state | $1.0 \times 10^2$ MΩ | $9.0 \times 10^2$ MΩ |

Figure 6:
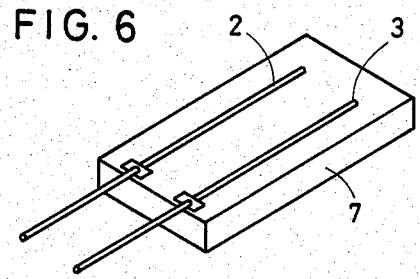
FIG. 6 is a perspective view illustrating still another example of sensing elements used in the present invention.
Figure 7:
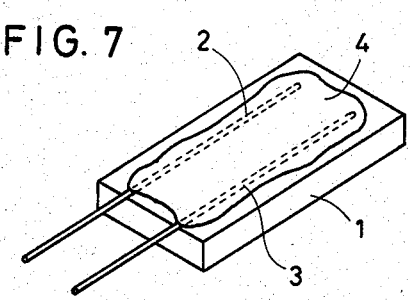
FIG. 7 is a perspective view illustrating further example of sensing elements used in the present invention.

Meanwhile, it is pointed out that the shape of the electrodes provided for the sensing element is not restricted to the comb-shape shown in FIGS. 4 and 5, and the electrodes may be the opposing electrodes having merely split-like shape as shown in FIGS. 6 and 7.

Another sensing element was produced in the same way as those of Examples 1 and 2 by using ceramics having composition shown in Table II. The change in the impedance between the electrodes of each of the produced elements, in the three states, dry, bedewed and frosted states, was measured. The measured results are also shown in Table II.

TABLE II

| Sample No. | Composition of the Sensing Element (percent by weight) | Resistance Value in the Dry State (MΩ) | Resistance Value in the Bedewed State (KΩ) | Resistance Value in the Frosted State (MΩ) | ε |
|---|---|---|---|---|---|
| 1 | MgTiO$_3$ (Ilmenite) | 6 × 10$^3$ | 170 | 1.2 × 10$^2$ | 16 |
| 2 | MgTiO$_3$ (86) + (Ilmenite) Mg$_2$TiO$_4$ (14) (Spinel) | 7 × 10$^3$ | 200 | 1.4 × 10$^2$ | 20 |
| 3 | MgTiO$_3$ (80) + (Ilmenite) CaTiO$_3$ (20) (Perovskite) | 6 × 10$^2$ | 230 | 1.5 × 10$^2$ | 35 |
| 4 | MgTiO$_3$ (91.2) + (Ilmenite) SrTiO$_3$ (8.8) (Perovskite) | 8 × 10$^2$ | 195 | 1 × 10$^2$ | 30 |
| 5 | ZnTiO$_3$ (90) + (Ilmenite) ZnTiO$_4$ (10) (Spinel) | 5 × 10$^3$ | 250 | 1 × 10$^2$ | 20 |
| 6 | MgTiO$_3$ (96) + (Ilmenite) ZnTiO$_3$ (4) (Ilmenite) | 6 × 10$^3$ | 200 | 1.2 × 10$^2$ | 17 |
| 7 | MgTiO$_3$ (94) + CaTiO$_3$ (6) | 7 × 10$^3$ | 88 | 1 × 10$^2$ | 19 |
| 8 | BaTiO$_3$ (50) − TiO$_2$ (50) System | 7 × 10$^2$ | 200 | 1.2 × 10$^2$ | 35 |
| 9 | Talc (63) − MgO (34) − BaTiO$_3$ (3) | 7 × 10$^3$ | 100 | 1 × 10$^2$ | 8 |
| 10 | MgTiO$_3$ (60) − SrTiO$_3$ (10) − BaTiO$_3$ (30) System | 7 × 10$^2$ | 120 | 1.4 × 10$^2$ | 40 |
| 11 | BaO (4) − TiO$_2$ (38) − NdO3/2 (58) System | 8 × 10$^2$ | 250 | 1.4 × 10$^2$ | 45 |
| 12 | MgO SiO$_2$ (Steatite) | 7 × 10$^3$ | 200 | 1 × 10$^2$ | 6 |
| 13 | 2MgO SiO$_2$ (Forsterite) | 6 × 10$^3$ | 100 | 1 × 10$^2$ | 6 |

As apparent from Table II, each of the dew and frost sensors which employ the respective sensing elements having the respective composition of the sample Nos. 1 to 13, indicates impedance between the electrodes thereof having the much changed value in the three states, or the dry, bedewed and frosted states. Thus, it is understood that it is possible to accurately detect the three states, the dry, bedewed and frosted states by using each of the sensing elements having the respective compositions described in Table II.

The present invention is achieved by using a sensing element whose value of resistance changes in the three states, dry, bedewed and frosted states as described above. In order to sense the three states with higher accuracy, it is necessary that the permittivity of the base material is lower than that of ice ($\epsilon = 80$). Because the frost adhering to the base material in the frosted state has the same permittivity as ice, there would be no difference between the resistance values in the dry state and in the frosted state if the permittivity of the base material is not lower than that of ice.

Figure 8:
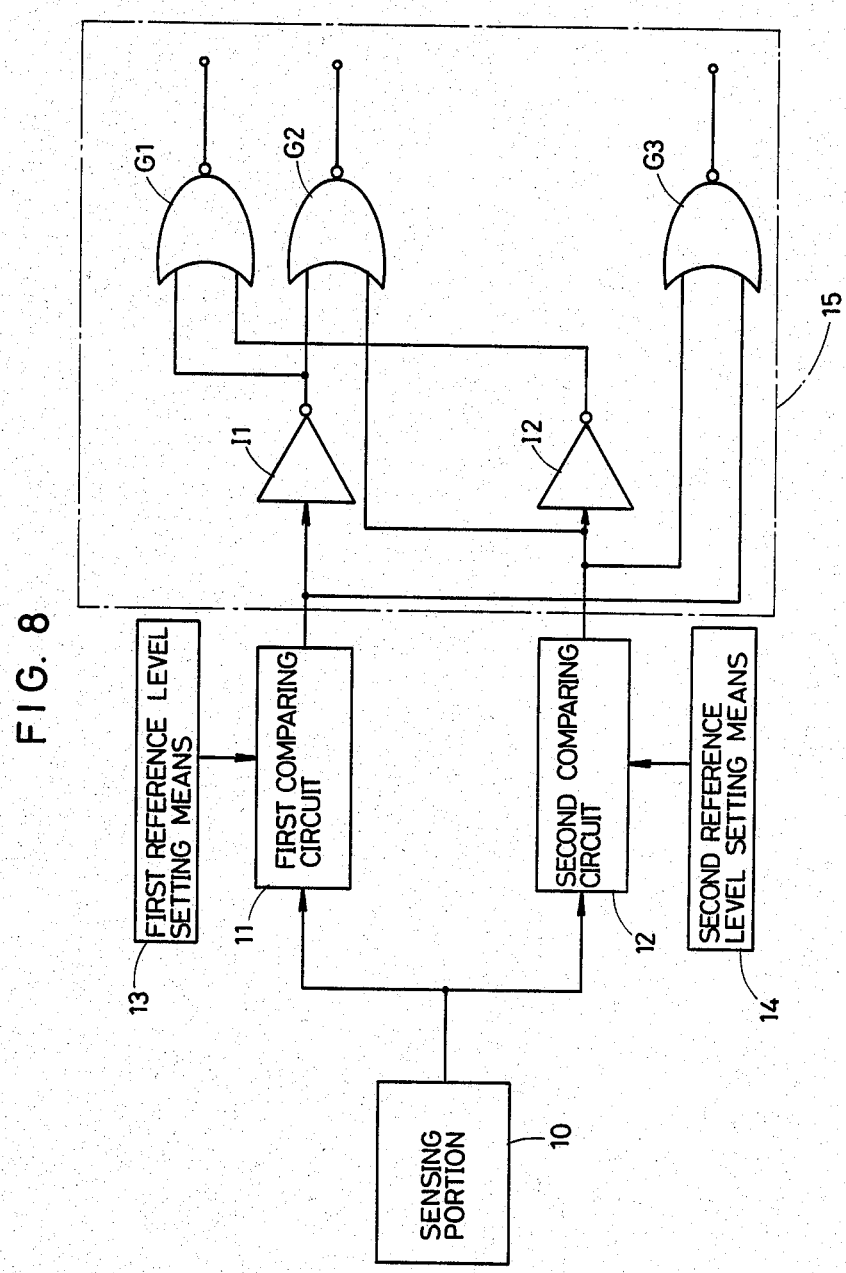
FIG. 8 is a block diagram showing one embodiment of the present invention.

FIG. 8 is a block diagram for explaining one embodiment of the present invention. Referring to FIG. 8, the embodiment comprises a sensing portion 10, two comparing circuits 11 and 12 provided with outputs from the sensing portion 10, first reference level setting means 13 for inputting a first reference level signal as a signal to be compared to the comparing circuit 11, second reference level setting means 14 for inputting a second reference level signal as a signal to be compared to the comparing circuit 12, and a determining circuit 15 (a portion encircled by a broken line) for determining which state of the three states, dry, bedewed and frosted states an atmosphere is in, responsive to outputs from the comparing circuits 11 and 12.

The sensing element 10 includes the element shown in FIG. 2 through 7, for example, outputs a signal corresponding to the impedance which changes in three states, or dry, bedewed and frosted states, as shown in FIG. 1. The output from the sensing element 10 is divided to be provided for the first comparing circuit 11 as first comparing means and the second comparing circuit 12 as second comparing means. To the first comparing circuit 11 is inputted the first reference level signal by the first reference level setting means. The first reference level of the signal is set between the impedance of the sensing element 10 in the bedewed state and the impedance of the sensing element 10 in the frosted state as apparently seen from FIG. 1. The first comparing circuit 11 compares the impedance of the sensing element 10 with the first reference level, and outputs a high level signal when the impedance of the sensing element 10 is higher than the first reference level and outputs a low level signal when the impedance of the sensing element 10 is lower than the same. On the other hand, to the second comparing circuit 12 is inputted the second reference level signal by the second reference level setting means. The second reference level of the signal is set between the impedance of the sensing element 10 in the dry state and the impedance of the sensing element 10 in the frosted state. The second comparing circuit 12 compares the impedance of the sensing element 10 with the second reference level, and outputs a high level signal when the impedance of the sensing element 10 is higher than the second reference level and outputs a low level signal when the impedance of the sensing element 10 is lower than the same.

As described above, the first and second comparing circuits 11 and 12 each output a high level or low level signal responsive to the change of the impedance of the sensing element 10. The outputs from the respective comparing circuits 11 and 12 are shown in the following TABLE III as apparent from relationship shown in FIG. 1. In the TABLE III, H represents a high level signal and L represents a low level signal.

TABLE III

|  | First Comparing Circuit 11 | Second Comparing Circuit 12 |
|---|---|---|
| Dry State | H | H |
| Frosted State | H | L |
| Bedewed State | L | L |

The outputs from the first and second comparing circuit 11 and 12 are provided for the determining circuit 15 as described above. The determining circuit 15 comprises two inverter I1, I2, and three NOR gates G1, G2, G3. The output from the first comparing circuit 11 is applied to the input terminal of the inverter I1 and one of input terminals of the NOR gate G3. The output from the inverter I1 is applied to each of one input terminals of the NOR gate G1 and G2. On the other hand, the output from the second comparing circuit 12 is applied to the input terminal of the inverter I2, the other terminal of the NOR gate G2 and the other terminal of the NOR gate G3. The output from the inverter I2 is applied to the other input terminal of the NOR gate G1. Meanwhile, the determining circuit 15 employs positive logic.

The determining circuit structured as described above determines which state of the three states, or dry, bedewed and frosted states an atmosphere is in, in the following way.

On the occasion of the dry state, as apparent from TABLE II, each of the comparing circuit 11 and 12 output a high level signal. The high level signal from the first comparing circuit 11 is applied to the inverter I1 and NOR gate G3. The high level signal inputted to the inverter I1 is inverted to a low level signal and then applied to the NOR gates G1 and G2. On the other hand, the high level signal from the second comparing circuit 12 is applied to the inverter I2, NOR gate G2 and NOR gate G3. The high level signal inputted to the inverter I2 is inverted to a low level signal to be applied to the NOR gate G1. As described above, on the occasion of the dry state, only the NOR gate G1 is provided with low level signals at both of the input terminals thereof. Accordingly, only the NOR gate G1 outputs a signal.

On the occasion of the sensing element 10 being in the frosted state, as apparent from TABLE III, the first comparing circuit 11 outputs a high level signal and the second comparing circuit 12 outputs a low level signal. The high level signal from the first comparing circuit 11 is applied to the inverter I1 and NOR gate G3. The high level signal inputted to the inverter I1 is inverted to a low level signal to be applied to the NOR gates G1 and G2. On the other hand, the low level signal from the second comparing circuit 12 is applied to the inverter I2, NOR gate G2 and NOR gate G3. The low level signal inputted to the inverter I2 is inverted to a high level signal to be applied to the NOR gate G1. As described above, on the occasion of the frosted state, only the NOR gate G2 is provided with low level signals in both of the input terminals thereof. Accordingly, only the NOR gate G2 outputs a signal.

On the occasion of the sensing element 10 being in the bedewed state, the first and second comparing circuits 11 and 12 both output low level signals. The low level signal from the first comparing circuit 11 is applied to the inverter I1 and NOR gate G3. The low level signal inputted to the inverter I1 is inverted to a high level signal to be applied to the NOR gate G1 and the NOR gate G2. On the other hand, the low level signal from the second comparing circuit 12 is applied to the inverter I2, NOR gate G2 and NOR gate G3. The low level signal inputted to the inverter I2 is inverted to a high level signal to be applied to the NOR gate G1. As described above, on the occasion of the bedewed state, only the NOR gate G3 is provided with low level signals at both of the input terminals thereof. Accordingly, only the NOR gate G3 outputs a signal.

As seen apparently from the above description, the NOR gate G1 outputs a signal on the occasion of the dry state, the NOR gate G2 outputs a signal on the occasion of the frosted state, and the NOR gate G3 outputs a signal on the occasion of the bedewed state. Accordingly, it is possible to determine which state of the three states, or dry, bedewed and frosted states the atmosphere is in.

Figure 9:
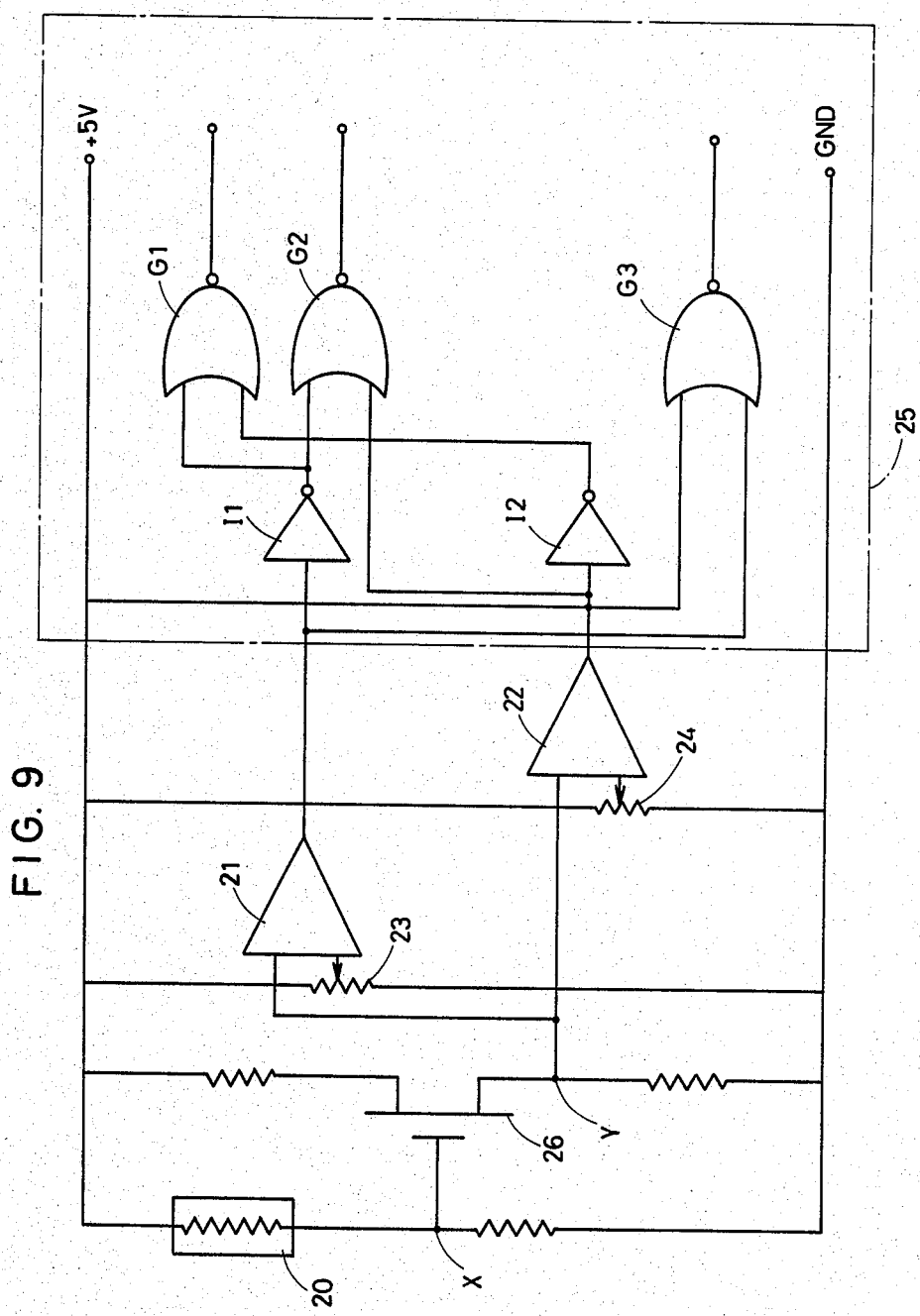
FIG. 9 is a circuit diagram more specifically illustrating the block diagram of FIG. 8.
Figure 10:
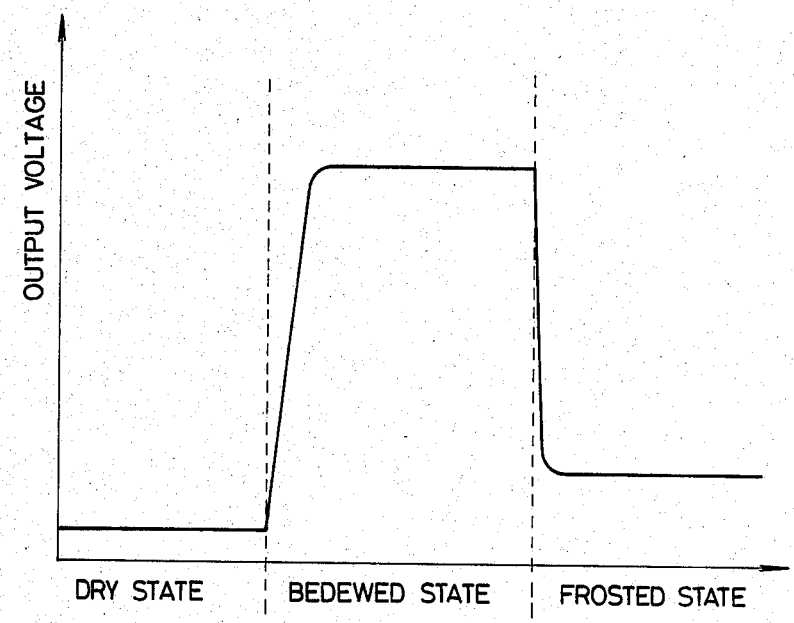
FIG. 10 is a view showing an outputted voltage at a connection point X of the circuit shown in FIG. 9.
Figure 11:
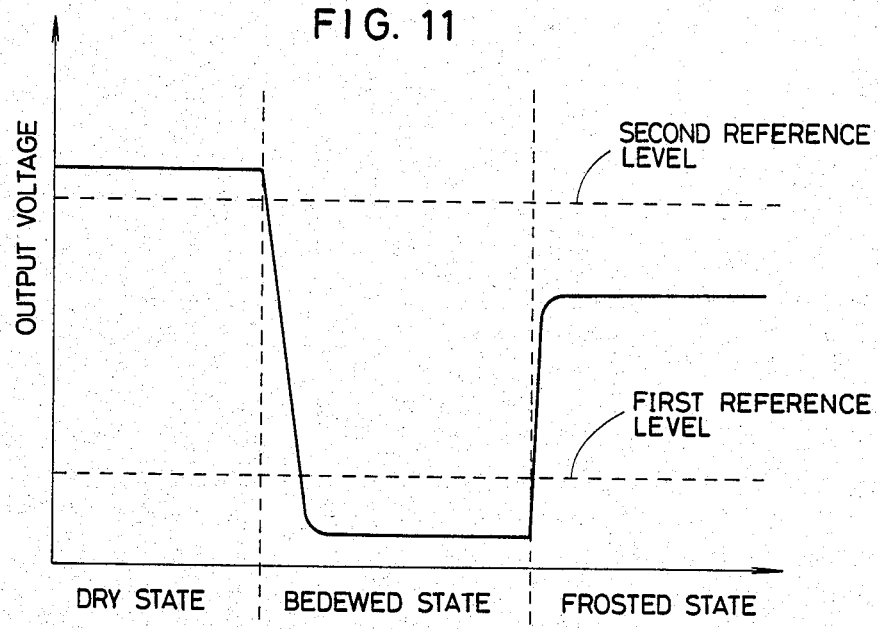
FIG. 11 is a view showing an outputted voltage at a connection point Y of the circuit shown in FIG. 9.

FIG. 9 is a circuit diagram for more specifically illustrating the embodiment shown in FIG. 8. FIGS. 10 and 11 are views for explaining an operation of the circuit in FIG. 9.

The circuit shown in FIG. 9 basically comprises a sensing element 20, an MOS-FET 26, comparators 21 and 22, and a determining circuit 25 (a portion encircled by a broken line) which is similar to the determining circuit 15 in FIG. 8. The impedance of the sensing element 20 changes in the three states, or dry, bedewed and frosted states, as shown in FIG. 1. Since the impedance of the sensing element 20 changes, voltage responsive to the change is inputted to the gate terminal of the MOS-FET 26. The input is amplified and inverted by the MOS-FET 26 to be inputted to operation amplifiers 21 and 22. To the operation amplifiers 21 and 22 are inputted the first and second reference level voltages through variable resistors 23 and 24, respectively. The outputs from the operation amplifiers 21 and 22 are applied to the determining circuit 25. Since the configuration of the determining circuit 25 is similar to that of the determining circuit 15 shown in FIG. 8, the corresponding component is denoted by the same reference numeral as that of FIG. 8 and explanation of the component is omitted.

Since the impedance of the sensing element 20 in the circuit of FIG. 9 structured as the above changes in the three states, or dry, bedewed and frosted states, the sensing element 20 outputs voltage which changes based on the impedance thereof. The change of voltage in the connection point X of the circuit in FIG. 9 is shown in FIG. 10. The outputted voltage from the sensing element 20 is amplified and inverted by the MOS-FET 26 and then outputted therefrom. The outputted voltage, that is the voltage at the connection point Y of FIG. 9, is shown in FIG. 11. As apparent from FIG. 11, the outputted voltage at the connection point Y has the maximum value in the dry state, the minimum value in the bedewed state, and the middle value in the frosted state. The outputted voltage from the MOS-FET 26 is inputted to the operation amplifiers 21 and 22. On the other hand, to the operation amplifiers 21 and 22 are inputted the first and second reference level voltages, respectively, whose levels are set through the variable resistors 23 and 24, respectively. The value of the first and second reference level voltages are selected as shown in FIG. 11. More specifically, the value of the first reference level voltage is selected between those of the outputted voltage in the frosted state and the outputted voltage in the bedewed state, and the value of the second reference level voltage is selected between those of the outputted voltage in the dry state and the outputted voltage in the frosted state. The operation amplifiers 21 and 22 compare the outputted voltage of the MOF-FET 26, with the first reference level voltage and the second reference level voltage, respectively. Thus, the change in the impedance of the sensing element 20 is detected in the form of the change in the voltage. Each of the operation amplifiers 21 and 22 outputs a high level signal when the outputted voltage from the MOS-FET 26 is higher than the respective reference level voltages and outputs a low level signal when the outputted voltage is lower than the same. The outputted signals from the operation amplifiers 21 and 22 are similar to the outputted true value from the comparing circuits 11 and 12 of FIG. 8 shown in TABLE III, respectively. The outputted signals from the operation amplifiers 21 and 22 are each inputted to the determining circuit 25. Meanwhile, since the operation of the determining circuit 25 is similar to that of the determining circuit 15 in FIG. 8, the explanation is omitted.

Each of the circuits shown in FIGS. 8 and 9 is merely one embodiment of the present invention. Accordingly, it is pointed out that the first and second comparing circuits and the determining circuit can be modified in various ways within the scope and spirit of the present invention.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for sensing dry, bedewed and frosted states, comprising:
    a sensing element including a base material having a permeativity which is less than the permeativity of ice and a pair of electrodes coupled to said base material at spaced locations thereof, the impedance of said sensing element as measured across said electrodes varying as a function of whether said sensing element is in the dry, bedewed or frosted states, said impedance being at a maximum value when said sensing element is in the dry state, said impedance being at a middle value lower than said maximum value when said sensing element is in the frosted state, said impedance being at a minimum value lower than said maximum and minimum values when said sensing element is in the bedewed state; and
    means for measuring the impedance between said electrodes and generating electric signals indicative of whether said sensing element is in the dry, bedewed or frosted state.

2. An apparatus in accordance with claim 1, wherein said impedance measuring means comprises:
    first reference level setting means for setting a first reference level which resides between said middle value and the minimum value of said impedance between said electrodes;
    second reference level setting means for setting a second reference level which resides between said middle value and the maximum value of said impedance between said electrodes;
    first comparing means for comparing said first reference level provided by said first reference level setting means with said impedance between the electrodes of said sensing element;
    second comparing means for comparing said second reference level provided by said second reference level setting means with the impedance between the electrodes of said sensing element; and
    determining means for determining that the dry state exists when said first comparing means indicates that the impedance between said electrodes is higher than said first reference level and said second comparing means indicates that the impedance between said electrodes is higher than said second reference level, for determining that the frosted state exists when said first comparing means indicates that the impedance between said electrodes is higher than said first reference level and said second comparing means indicates that the impedance between said electrodes is lower than said second reference level, and for determining that the bedewed state exists when said first comparing means indicates that the impedance between said electrodes is lower than said first reference level and said second comparing means indicates that the impedance between said electrodes is lower than said second reference level.

3. An apparatus in accordance with claim 1 or 2, wherein
    said base material includes a ceramic substrate, and said electrodes are arranged on said ceramic substrate.

4. An apparatus in accordance with claim 1 or 2, wherein
    said base material includes a resistive film arranged on an isolating substrate, and wherein said electrodes are arranged on said isolating substrate such that at least a part of said electrodes is covered with said resistive film.

5. An apparatus in accordance with claim 1 or 2, wherein the impedance between said electrodes is:
    defined in said dry state primarily as a function of said resistance of said base material;
    defined in said frosted state primarily as a function of the permittivity of ice forming frost on said base material; and
    defined in said bedewed state primarily as a function of an ionic conduction through dew formed on said base material.

6. An apparatus in accordance with claim 2, wherein said first comparing means and said second comparing means each include an operation amplifier.

7. An apparatus in accordance with claim 2, wherein said determining means includes a gating means.

8. An apparatus in accordance with claim 3, wherein the impedance between said electrodes is:
    defined in said dry state primarily as a function of said resistance of said base material;
    defined in said frosted state primarily as a function of the permittivity of ice forming frost on said base material; and
    defined in said bedewed state primarily as a function of an ionic conduction through dew formed on said base material.

9. An apparatus in accordance with claim 4, wherein the impedance between said electrodes is:
    defined in said dry state primarily as a function of said resistance of said base material;
    defined in said frosted state primarily as a function of the permittivity of ice forming frost on said base material; and
    defined in said bedewed state primarily as a function of an ionic conduction through dew formed on said base material.

* * * * *